United States Patent [19]

Kirkpatrick

[11] 4,151,167
[45] Apr. 24, 1979

[54] 5-ACYLAMINO-1,3,4-THIADIAZOLE-2-SULFONAMIDES

[75] Inventor: Joel L. Kirkpatrick, Overland Park, Kans.

[73] Assignee: Gulf Oil Corporation, Pittsburgh, Pa.

[21] Appl. No.: 839,671

[22] Filed: Oct. 5, 1977

Related U.S. Application Data

[62] Division of Ser. No. 743,543, Nov. 22, 1976, Pat. No. 4,097,263.

[51] Int. Cl.² .................... C07D 285/12; A01N 9/16; A01N 9/22
[52] U.S. Cl. ............................................ 260/306.8 D
[58] Field of Search .................................. 260/306.8 D

[56] References Cited

FOREIGN PATENT DOCUMENTS 508982 1/1955 Canada ............................ 260/306.8 D
225412 12/1957 Australia ......................... 260/306.8 D

OTHER PUBLICATIONS

Gray et al., J. Pharmacol. Exptl. Therap., vol. 121, pp. 160–170 (1957).
Klosa, Chem. Abstracts, vol. 53, Cols. 9199–9200 (1953).

Primary Examiner—Alton D. Rollins
Attorney, Agent, or Firm—Carl A. Cline

[57] ABSTRACT

Compounds which are useful as selective herbicides have the general structural formula

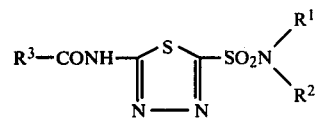

in which $R^1$ and $R^2$ are selected from hydrogen, and lower alkyl, alkenyl, alkylene and alkoxy structures and together possess a total of 1 to 6 carbon atoms when $R^3$ is ethyl, propyl, isopropyl, cyclopropyl, methoxy or tert-butyl.

8 Claims, No Drawings

5-ACYLAMINO-1,3,4-THIADIAZOLE-2-SULFONAMIDES

This is a division of U.S. Ser. No. 743,543, filed Nov. 22, 1976, now U.S. Pat. No. 4,097,263.

DESCRIPTION OF THE INVENTION

Background of the Invention

Compounds of the general structural formula

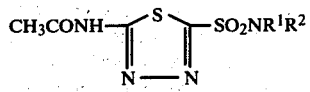

have been disclosed as intermediates employed in the synthesis of ureidothiadiazolesulfonamide herbicides, for example, in U.S. Pat. No. 3,824,247. The above-illustrated acetamido-substituted compounds are generally not significantly phytotoxic. For example, the compounds having the above structural formula in which both $R^1$ and $R^2$ are both propyl substituents, or in which $R^1$, $R^2$ and the nitrogen atom together form a piperidinyl structure appear to possess no useful phytotoxicity. I have discovered useful herbicidal properties in only two acetamido compounds of the general structural formula illustrated above. However, when the acetyl group is replaced by other substituents the character of the compounds is changed substantially. I have discovered that a class of compounds which are useful selective herbicides are those having the general structural formula

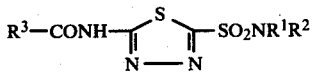

in which $R^1$ and $R^2$ are selected from hydrogen, and lower alkyl, alkenyl, alkylene and alkoxy structures and together possess a total of 1 to 6 carbon atoms when $R^3$ is ethyl, propyl, isopropyl, cyclopropyl, methoxy or tert-butyl. A particularly useful compound of the group is one in which $R^1$ is H, $R^2$ is methyl and $R^3$ is cyclopropyl. This compound is useful in a special problem situation, combating specific weeds in sugar beets.

SYNTHESIS OF THE HERBICIDES

Synthesis of the compounds is illustrated by means of the following procedures:

PREPARATION OF 2-PROPIONAMIDO-5-MERCAPTO-1,3,4-THIADIAZOLE

To a suspension of 20 g of 2-amino-5-mercapto-1,3,4-thiadiazole in 200 ml of pyridine was added 14.6 g of propionyl chloride with cooling over a five minute period. After stirring the reaction mixture for 4 hours at room temperature, water was added and the resulting solid collected by filtration to give 20.2 g of 2-propionamido-5-mercapto-1,3,4-thiadiazole, m.p. 234°–237° C.

PREPARATION OF 2-PROPIONAMIDO-5-(N-METHYL-N-ETHYL-SULFONAMIDO)-1,3,4-THIADIAZOLE

A slurry of 5.0 g of 2-propionamido-5-mercapto-1,3,4-thiadiazole in 150 ml of 5% NaCl solution was cooled to 0° and chlorine gas slowly bubbled through for about 1 hr. with rapid stirring. The temperature was maintained at 0°–5° during the reaction. The resulting solid was collected by filtration, washed with ice water, then resuspended in 100 ml of ice water. An excess of methylethylamine was added and the resulting solution stirred for 30 min. Acidification to pH 1 with dilute hydrochloric acid gave a solid which was isolated by filtration, washed with water and dried, 5.2 g, m.p. 208°–210° C., and was identified as the desired product, 2-propionamido-5-(N-methyl-N-ethylsulfonamido)-1,3,4-thiadiazole.

The aminomercaptothiadiazole starting material may be readily made by means of published procedures.

Illustrative compounds made by means of the general method illustrated above are those listed in the following table.

| Compound | $R^1$ | $R^2$ | $R^3$ | M.P.(° C.) |
|---|---|---|---|---|
| 1 | CH₃ | H | —CH(CH₃)₂ | 219–221 |
| 2 | CH₃ | CH₃ | —CH(CH₃)₂ | 233–237 |
| 3 | CH₃ | CH₃ | CH₂CH₃ | 235–238 |
| 4 | CH₃ | H | CH₂CH₃ | 224–226 |
| 5 | CH₂CH₃ | CH₂CH₃ | CH₂CH₃ | 203–205 |
| 6 | H | H | CH₂CH₃ | 253–254 (dec) |
| 7 | CH₃ | CH₃ | cyclopropyl | 248–250 |
| 8 | CH₃ | H | " | 215–217 |
| 9 | CH₂CH₃ | CH₂CH₃ | " | 185–195 |
| 10 | H | H | " | 264–266 (dec) |
| 11 | CH₃ | CH₃ | CH₃ | 267–270 |
| 12 | CH₃ | H | CH₃ | 263–265 |
| 13 | CH₂CH₃ | H | cyclopropyl | 194–195 |
| 14 | CH₃ | OCH₃ | " | 211–215 |
| 15 | —CH(CH₃)₂ | H | " | 210–215 |
| 16 | CH₂CH₂CH₃ | H | " | 231–233 |
| 17 | tetramethylene | | " | 232–234 |
| 18 | OCH₃ | H | " | 205–207 |
| 19 | CH₃ | n-C₄H₉ | " | 166–167 |
| 20 | 1,4-dimethyltetramethylene | | " | 257–260 |
| 21 | CH₃ CH₂=C—CH₂— | H | " | 203–206 |
| 22 | CH₂CH₃ | H | —CH(CH₃)₂ | 205–206 |
| 23 | CH₂CH₃ | CH₂CH₃ | " | 203–211 |
| 24 | —CH(CH₃)₂ | H | " | 229–232 |
| 25 | tert-butyl | H | " | 236–239 (dec) |
| 26 | CH₃ | n-C₄H₉ | " | 158–161 |
| 27 | CH₃ | sec-C₄H₉ | " | 146–151 |
| 28 | CH₃ | CH₂CH₃ | " | 203–205 |
| 29 | CH₃ | C₂H₅ | cyclopropyl | 170–172 |
| 30 | CH₃ | sec-C₄H₉ | " | 152–155 |
| 31 | CH₃ | CH₂CN | " | 222–224 (dec) |
| 32 | tert-butyl | H | " | 249–253 (dec) |
| 33 | CH₃ | CH₃ | tert-butyl | 175–177 |
| 34 | CH₃ | CH₃ | OCH₃ | 205–207 (dec) |
| 35 | CH₃ | CH₂CH₃ | CH₂CH₃ | 208–210 |

COMBATING UNWANTED VEGETATION

Post-emergent use of the herbicides to combat unwanted vegetation may be demonstrated by means of the procedure described below.

POST-EMERGENT USE

An aqueous dispersion of each active compound is prepared, for example, by combining 0.4 gram of the compound with about 4 ml of a solvent-emulsifier mixture (3 parts of a commercial polyoxyethylated vegetable oil emulsifier, one part xylene, one part kerosene) and then adding water, with stirring, to a final volume of 40 ml. Rate of application and spray volume may be adjusted by appropriate dilution. The species of plants of which each compound is to be tested are planted in disposable 12 in.×10 in. greenhouse flats about 3 in. deep. Twelve days after emergence of the plants, each flat is sprayed with an aqueous dispersion of the active compound prepared as described above, at chosen rates of active compound per acre and at a spray volume of 40 gallons per acre. Approximately two weeks after the spray application the plants are observed and the results rated according to the following schedule.

DEGREE OF EFFECT

0 = no effect
1 = slight effect (observable, but no permanent injury)
2 = moderate effect (some plants died)
3 = severe effect (most of the plants died)
4 = maximum effect (all plants died)

Pre-emergent use of the herbicides to combat vegetation may be demonstrated by means of the procedure described below.

PRE-EMERGENT USE

A solution of each active compound is prepared by dissolving 290 mg of the compound in 200 ml of acetone. Disposable expanded polystyrene trays about 2½ inches deep and about one square foot in area are filled with soil, seeded and sprayed with the solution at the chosen rate of active chemical per acre of sprayed area. Twenty-eight days after seeding and treatment the plantings are examined and herbicidal effects are rated according to the schedule as described above.

Results of both post-emergent application at 5 lb. per acre and pre-emergent use at 10 lb. per acre are tabulated below.

Results of Herbicidal Use

| Compound No. | | Crabgrass | Coxcomb | Downy brome | Millet | Alfalfa | Oats | Radish | Sugarbeet | Tomato |
|---|---|---|---|---|---|---|---|---|---|---|
| 1 | pre | 4 | 4 | 4 | 4 | | | 4 | 4 | |
|   | post |   |   |   | 3 | 3 | 2 | 4 | 4 | 4 |
| 2 | pre | 4 | 4 | 4 | 4 | | | 4 | 4 | |
|   | post |   |   |   | 4 | 4 | 2 | 4 | 4 | 4 |
| 3 | pre | 4 | 4 | 4 | 4 | | | 4 | 4 | |
|   | post |   |   |   | 4 | 4 | 2 | 4 | 4 | 4 |
| 4 | pre | 4 | 4 | 4 | 4 | | | 4 | 4 | |
|   | post |   |   |   | 3 | 3 | 2 | 4 | 4 | 4 |
| 5 | pre | 4 | 4 | 4 | 4 | | | 4 | 4 | |
|   | post |   |   |   | 3 | 3 | 2 | 4 | 4 | 4 |
| 6 | pre | 2 | 4 | 0 | 3 | | | 3 | | |
|   | post |   |   |   | 0 | 0 | 0 | 1 | 2 | 1 |
| 7 | pre | 4 | 4 | 4 | 4 | | | 4 | 4 | |
|   | post |   |   |   | 4 | 4 | 4 | 4 | 4 | 4 |
| 8 | pre | 4 | 4 | 4 | 4 | | | 4 | 4 | |
|   | post |   |   |   | 4 | 4 | 4 | 4 | 4 | 4 |
| 9 | pre | 4 | 4 | 4 | 4 | | | 4 | 4 | |
|   | post |   |   |   | 4 | 4 | 3 | 4 | 4 | 4 |
| 10 | pre | 2 | 3 | 1 | 3 | | | 3 | | |
|    | post |   |   |   | 0 | 0 | 0 | 1 | 2 | 0 |
| 11 | pre | 3 | 4 | 4 | 4 | | | 4 | 4 | |
|    | post |   |   |   | 1 | 2 | 1 | 3 | 4 | 4 |
| 12 | pre | 3 | 4 | 1 | 3 | | | 4 | | |
|    | post |   |   |   | 1 | 1 | 1 | 4 | 2 | 4 |
| 13 | pre | 4 | 3 | 3 | 4 | | | 4 | 4 | |
|    | post |   |   |   | 4 | 4 | 3 | 4 | 4 | 4 |
| 14 | pre | 3 | 4 | 2 | 3 | | | 4 | 4 | |
|    | post |   |   |   | 4 | 4 | 2 | 4 | 4 | 4 |
| 15 | pre | 3 | 4 | 2 | 4 | | | 4 | 4 | |
|    | post |   |   |   | 4 | 4 | 2 | 4 | 4 | 4 |
| 16 | pre | 2 | 3 | 2 | 3 | | | 4 | 4 | |
|    | post |   |   |   | 3 | 3 | 2 | 3 | 4 | 4 |
| 17 | pre | 3 | 4 | 1 | 4 | | | 4 | 4 | |
|    | post |   |   |   | 4 | 4 | 1 | 4 | 4 | 4 |
| 18 | pre | 4 | 2 | 2 | 3 | | | 3 | 4 | |
|    | post |   |   |   | 3 | 4 | 2 | 4 | 4 | 4 |
| 19 | pre | 3 | 4 | 4 | 3 | | | 4 | 4 | |
|    | post |   |   |   | 4 | 4 | 2 | 4 | 4 | 4 |
| 20 | pre | 1 | 4 | 4 | 1 | | | 4 | 4 | |
|    | post |   |   |   | 2 | 3 | 1 | 4 | 4 | 2 |
| 21 | pre | 2 | 4 | 4 | 2 | | | 4 | 4 | |
|    | post |   |   |   | 2 | 3 | 1 | 2 | 4 | 3 |
| 22 | pre | 1 | 4 | 4 | 1 | | | 4 | 4 | |
|    | post |   |   |   | 2 | 3 | 1 | 4 | 4 | 2 |
| 23 | pre | 2 | 4 | 4 | 2 | | | 4 | 4 | |
|    | post |   |   |   | 2 | 3 | 1 | 2 | 4 | 3 |
| 24 | pre | 3 | 4 | 2 | 4 | | | 4 | 4 | |
|    | post |   |   |   | 0 | 1 | 0 | 1 | 4 | 1 |
| 25 | pre | 0 | 4 | 3 | 2 | | | 3 | 4 | |
|    | post |   |   |   | 0 | 0 | 0 | 1 | 1 | 0 |
| 26 | pre | 0 | 4 | 1 | 1 | | | 4 | 4 | |
|    | post |   |   |   | 2 | 3 | 1 | 4 | 4 | 4 |
| 27 | pre | 0 | 4 | 3 | 1 | | | 4 | 4 | |
|    | post |   |   |   | 1 | 2 | 1 | 4 | 4 | 4 |

-continued

| Compound No. | | Crabgrass | Coxcomb | Downy brome | Millet | Alfalfa | Oats | Radish | Sugarbeet | Tomato |
|---|---|---|---|---|---|---|---|---|---|---|
| 28 | pre | 4 | 4 | 4 | 4 | | | 4 | 4 | |
| | | | | | 2 | 4 | 3 | 4 | 4 | 4 |
| 29 | pre | 4 | 4 | 4 | 4 | | | 4 | 4 | |
| | post | | | | 4 | 4 | 4 | 4 | 4 | 4 |
| 30 | pre | 3 | 4 | 4 | 2 | | | 4 | 4 | |
| | post | | | | 2 | 3 | 3 | 4 | 4 | 4 |
| 31 | pre | 0 | 4 | 1 | 0 | | | 2 | 4 | |
| | post | | | | 1 | 1 | 2 | 2 | 3 | 2 |
| 32 | pre | 4 | 4 | 4 | 4 | | | 4 | 4 | |
| | post | | | | 1 | 2 | 1 | 2 | 3 | 1 |
| 33 | pre | 4 | 4 | 4 | 4 | | | 4 | 4 | |
| | post | | | | 4 | 4 | 3 | 4 | 4 | 4 |
| 34 | pre | 4 | 4 | 4 | 4 | | | 4 | 4 | |
| | post | | | | 4 | 4 | 3 | 4 | 4 | 4 |
| 35 | pre | 4 | 4 | 4 | 4 | | | 4 | 4 | |
| | post | | | | 4 | 4 | 3 | 4 | 4 | 4 |

It will be noticed that in the results tabulated above, some compounds were so phytotoxic that no selectivity pattern was clearly evident. However, when the application rate is reduced and tests are conducted on a greater variety of species, useful selectivities appear. By way of illustration, at a post-emergent application rate of only one-half pound per acre, Compound No. 29 gives complete control of several species of weeds, including yellow foxtail, smartweed, velvet leaf, jimson weed and cocklebur without permanent injury to either soybeans or peanuts. It is advisable, of course, to conduct tests outdoors under realistic crop growth conditions, including variations in weather, before a judgment is made regarding potential commercial use of a herbicide. This is particularly advisable with respect to certain crops which do not behave the same outdoors as they do in a greenhouse. This is the case with sugar beets, as discussed below.

COMBATING WEEDS IN SUGAR BEETS

Weeds in sugar beets are particularly troublesome for a variety of reasons. Sugar beets are grown in twenty-three states of the U.S., from Maine to California, about 70 percent of the acreage being irrigated land. The wide area includes so many pestiferous weeds that no single herbicide can be expected to solve all of the weed control problems. The present practice is to use combinations of more than one herbicide at a time. In order to obtain effective weed control in this manner, a large choice of herbicides is needed. However, the choice of desirable selective herbicides for this purpose is inadequate. Unfortunately sugar beets are easily injured by the majority of herbicides and some of the worst weeds, such as kochia and lambsquarters are very similar in herbicide sensitivity to the crop.

One characteristic of sugar beets is beneficial in this situation, however. There is a tendency for the beets to produce a stand which is too thick for maximum crop yield and thinning of the stand is customary. Consequently, injury of a minor portion of the beet plants by the herbicide, for example, about ten percent, can be tolerated. In general, preemergence chemical weed control at planting time is preferred, so as to avoid the expense of making another pass through the field at a later date. Sugar beets exhibit behavior outdoors which is often different from that encountered in a greenhouse. One of the herbicides of this invention was tested outdoors at two locations, over one hundred miles apart so as to assess its performance under field conditions in combating weeds in sugar beets and various grain crops. The following procedure was used:

Various crop and weed species were seeded in 12 inch rows with Planet Jr. planters. Plots were 5 feet wide by 32 feet long with 1 or 2 replications.

Treatments were applied with a $CO_2$-pressurized hand sprayer. Three (3) Tee Jet 8003 nozzles on 20 inch spacings were operated at a speed of 3 mph through the field and at a pressure of 40 psi, resulting in a spray volume of 30 gallon per acre.

Preemergence applications were made on the day of planting while postemergence treatments were made 2 or 3 weeks after planting, depending upon the location. Commercial herbicides were included as standards for purposes of comparison.

Evaluations were made on a 0 to 10 scale. Where 0=no effect and 10=complete kill. A dash (—) indicates that a rating was not given due to a poor stand or the specie was over-grown by an uncontrolled volunteer specie, such as giant foxtail at the first location or pigweed at the second location.

Results are presented in the following table.

| | | Compound No. 8 Application Rate lb. per acre | | | | Ethofumesate lb. per acre (pre-emergent) | | | Phenmedipham lb. per acre (post-emergent) |
|---|---|---|---|---|---|---|---|---|---|
| Plant Species | | ½ | 1 | 2 | 4 | 1 | 2 | 4 | 1 |
| Giant Foxtail | pre | | 3,8 | 9,9 | 8,10 | 10,10 | 10,10 | 10,10 | |
| | post | 0,1 | 2,2 | 2,6 | | | | | 3,3 |
| Barnyard grass | pre | | 2,8 | 3,9 | 8,10 | 7,6 | 9,8 | 10,10 | |
| | post | 2,2 | 3,2 | 2,5 | | | | | 3,3 |
| Crabgrass | pre | | -,10 | 9,- | — | 10,10 | 10,- | — | |
| | post | — | — | — | | | | | 3,2 |
| Grain Sorghum | pre | | 0,2 | 2,5 | 3,6 | 3,2 | 4,5 | 10,5 | |
| | post | 2,3 | 0,0 | 0,2 | | | | | 3,2 |

RESULTS OF HERBICIDE TESTS AT TWO OUTDOOR LOCATIONS -continued

| Plant Species | | Compound No. 8 Application Rate lb. per acre | | | | Ethofumesate lb. per acre (pre-emergent) | | | Phenmedipham lb. per acre (post-emergent) |
|---|---|---|---|---|---|---|---|---|---|
| | | ½ | 1 | 2 | 4 | 1 | 2 | 4 | 1 |
| Wheat | pre | | 2,7 | 3,8 | 0,10 | 10,8 | 10,9 | 10,10 | 7,- |
| | post | — | — | — | | | | | |
| Oats | pre | | 0,1 | 0,7 | 3,10 | 6,6 | 9,8 | 10,10 | 1,- |
| | post | — | — | — | | | | | |
| Barley | pre | | 0,2 | 0,5 | 3,8 | 5,5 | 7,7 | 9,9 | 3,- |
| | post | — | — | — | | | | | |
| Rice | pre | | 0,2 | 0,4 | 0,7 | 2,3 | 5,7 | 10,10 | 3,- |
| | post | — | — | — | | | | | |
| Corn | pre | | 0,1 | 0,1 | 0,3 | 4,0 | 5,0 | 5,3 | 4,4 |
| | post | 3,0 | 0,0 | 0,3 | | | | | |
| Cocklebur | pre | | 0,0 | 0,0 | 0,- | 0,0 | 0,0 | 0,- | — |
| | post | 0,5 | -,8 | -,8 | | | | | |
| Velvetleaf | pre | | 1,2 | 0,4 | 0,5 | 0,3 | 4,4 | 5,5 | 2,0 |
| | post | 3,2 | 3,2 | 4,5 | | | | | |
| Morningglory | pre | | 0,2 | 0,5 | 0,9 | 0,0 | 3,2 | 4,3 | 3,3 |
| | post | 0,4 | 0,1 | 4,3 | | | | | |
| Wild Mustard | pre | | 0,7 | 0,9 | 10,10 | 3,5 | 9,4 | -,7 | 10,10 |
| | post | 10,3 | 10,0 | 10,5 | | | | | |
| Lambsquarters | pre | | 9,10 | 9,- | — | 5,- | 10,- | 10 | 10,- |
| | post | 10,- | 10,- | 10,- | | | | | |
| Redroot Pigweed | pre | | 8,10 | 10,10 | 10,10 | 10,10 | 10,10 | 10,10 | 8,8 |
| | post | 8,4 | 10,8 | 10,10 | | | | | |
| Soybeans | pre | | 0,1 | 0,2 | 2,4 | 4,3 | 4,3 | 6,4 | 2,- |
| (Clark) | post | -,2 | -,4 | -,5 | | | | | |
| Flax | pre | | 2,0 | 0,3 | 2,6 | 3,2 | 4,4 | 7,2 | 3,4 |
| | post | 1,1 | 6,2 | 10,6 | | | | | |
| Sunflower | pre | | 0,2 | 0,7 | 2,10 | 0,1 | 0,1 | 0,2 | 3,2 |
| | post | 4,2 | 9,6 | 10,7 | | | | | |
| Rape | pre | | 3,10 | 7,10 | 10,10 | 0,1 | 1,2 | 4,6 | 9,9 |
| | post | 7,0 | 10,2 | 10,6 | | | | | |
| Sugar Beet | pre | | 2,3 | 0,5 | 0,8 | 0,2 | 2,3 | 2,1 | 4,4 |
| | post | 2,0 | 6,3 | 5,5 | | | | | |
| Volunteer: | pre | | 10 | 10 | 10 | 7 | 10 | 10 | |
| Smartweed | post | 9 | 9 | 10 | | | | | |

In the outdoor tests described above, a rating from about 8 to 10 indicates weed control to a beneficial extent, sufficient to obtain improved yields of crops. An injury rating on the crop of zero to about 2 can usually be tolerated, if the weed infestation would otherwise be severe. The herbicide designated as Compound No. 8 herein has been shown to be particularly useful when applied pre- or post-emergently at a rate of from one-half to about one and one-half pounds per acre to control crabgrass, wild mustard, lambsquarters and redroot pigweed in the presence of such crops as corn, soybeans and sugar beets. Preferably, Compound No. 8 is applied pre-emergently at a rate of between one-half and one pound per acre to combat weeds such as lambsquarters and pigweed in sugarbeets.

I claim:

1. The compound having the structural formula

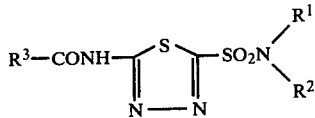

in which $R^1$ and $R^2$ are methyl and $R^3$ is cyclopropyl.

2. The compound having the structural formula

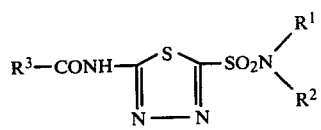

in which $R^1$ is methyl, $R^2$ is hydrogen and $R^3$ is cyclopropyl.

3. The compound having the structural formula

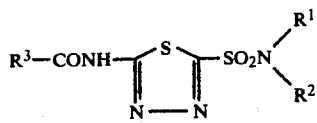

in which $R^1$ and $R^2$ are ethyl and $R^3$ is cyclopropyl.

4. The compound having the structural formula

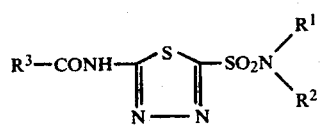

in which $R^1$ is ethyl, $R^2$ is hydrogen and $R^3$ is cyclopropyl.

5. The compound having the structural formula

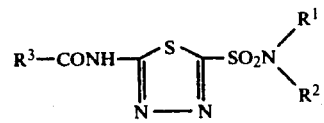

in which $R^1$ is methyl, $R^2$ is butyl and $R^3$ is cyclopropyl.

6. The compound having the structural formula in which R¹ is methyl, R² is ethyl and R³ is cyclopropyl.
7. The compound having the structural formula
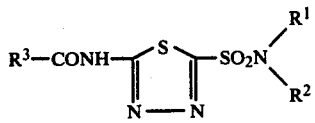
in which R¹ is methyl, R² is sec. butyl and R³ is cyclopropyl.
8. The compound having the structural formula
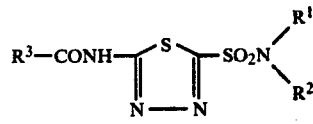
in which R¹ is tert-butyl, R² is hydrogen and R³ is cyclopropyl.
* * * * *